US00PP20271P2

(12) United States Plant Patent
Stewart

(10) Patent No.: US PP20,271 P2
(45) Date of Patent: Sep. 8, 2009

(54) ***ANIGOZANTHOS* HYBRID PLANT NAMED 'RAMBOBALL'**

(50) Latin Name: ***Anigozanthos* hybrid**
Varietal Denomination: Ramboball

(75) Inventor: Ian Angus Stewart, Somersby (AU)

(73) Assignee: Ramm Botanicals Holdings Pty., Ltd., Tüggerah, NSW (AU)

( * ) Notice: Subject to any disclaimer, the term of this patent is extended or adjusted under 35 U.S.C. 154(b) by 0 days.

(21) Appl. No.: 12/221,774

(22) Filed: Aug. 6, 2008

(51) Int. Cl.
*A01H 5/00* (2006.01)

(52) U.S. Cl. ..... Plt./362

(58) Field of Classification Search ..... Plt./362
See application file for complete search history.

(56) References Cited

OTHER PUBLICATIONS

Australian Plant Breeder's Rights Application No. 2008/120 filed Apr. 30, 2008 http://pbr.ipaustralia.plantbreeders.gov.au/.
Plant material first became available to the public on Aug. 22, 2007 in the form of an Australian sale.

*Primary Examiner*—Kent L Bell
(74) *Attorney, Agent, or Firm*—Audrey Charles

(57) ABSTRACT

A new and distinct cultivar of *Anigozanthos* hybrid plant named 'Ramboball', characterized by its medium red-colored flowers with a small to medium sized perianth tube, short to medium plant height with an upright growth habit, large number of infloresecences per plant, an almost continuous natural flowering season, medium degree of reflexing of perianth lobes on a mature flower, short flowering stem length and tolerance to alternaria and rust diseases.

1 Drawing Sheet

Latin name of genus and species of plant claimed: *Anigozanthos* hybrid.

Variety denomination: 'Ramboball'.

BACKGROUND OF THE INVENTION

The present invention relates to a new and distinct perennial variety of *Anigozanthos* hybrid, which has been given the variety denomination of 'Ramboball'. Its market class is that of an ornamental plant. 'Ramboball' is intended for use in landscaping and as a decorative plant.

The new cultivar originated in a controlled breeding program in Tuggerah, New South Wales, Australia during October 2002. The new *Anigozanthos* hybrid cultivar is the result of cross-pollination. The female (seed) parent of the new cultivar is an unnamed proprietary *Anigozanthos* hybrid breeding selection, not patented, characterized by its medium number of inflorescences produced per plant and a medium length of flowering season. The male (pollen) parent of the new cultivar is an unnamed proprietary *Anigozanthos* hybrid breeding selection, not patented, characterized by its medium number of inflorescences produced per plant and a medium length of flowering season. The new cultivar was discovered and selected as a single flowering plant within the progeny of the above stated cross-pollination during March 2006 in a controlled environment at Tuggerah, New South Wales, Australia.

Asexual reproduction of the new cultivar by in vitro propagation of micro-plants since June 2006 at Tuggerah, New South Wales, Australia has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Ramboball' as a new and distinct cultivar of *Anigozanthos* hybrid plant:

1. Medium red-colored flowers with a small to medium sized perianth tube;
2. Short to medium plant height with an upright growth habit;
3. Large number of infloresecences per plant;
4. An almost continuous natural flowering season;
5. Medium degree of reflexing of perianth lobes on a mature flower;
6. Short flowering stem length; and
7. Tolerance to alternaria and rust diseases.

Plants of the new cultivar differ from plants of the unnamed proprietary *Anigozanthos* hybrid breeding selection female and male parents primarily in having a greater number of infloresecences and a longer natural flowering season.

Of the many commercially available *Anigozanthos* hybrid cultivars, the most similar in comparison to the new cultivar is 'Bush Ranger', U.S. Plant Pat. No. 6,478. However, in side by side comparisons, plants of the new cultivar differ from plants of 'Bush Ranger' in at least the following characteristics:

1. Plants of the new cultivar have a larger number of infloresecences per plant than plants of 'Bush Ranger'; and
2. Plants of the new cultivar have a greater degree of reflexing of perianth lobes on a mature flower than plants of 'Bush Ranger'; and
3. Plants of the new cultivar have a shorter perianth tube length than plants of 'Bush Ranger'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Ramboball'.

DETAILED BOTANICAL DESCRIPTION

Figure 1:
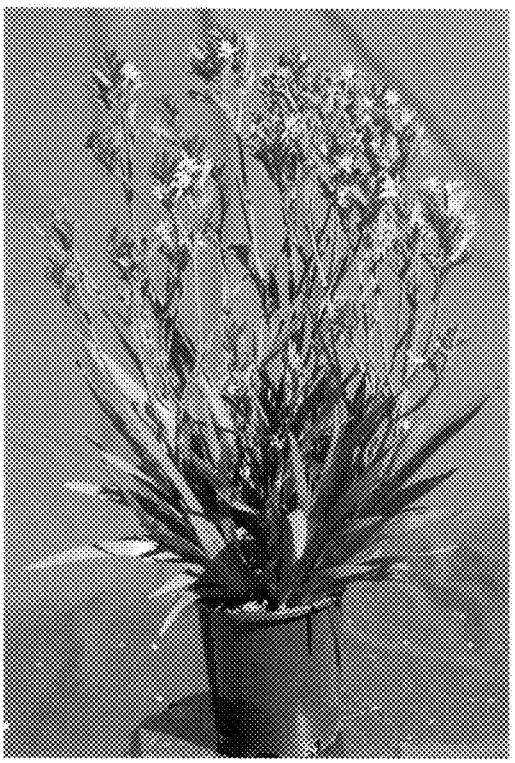
FIG. 1 illustrates a 'Ramboball' plant in a 14 cm pot grown for approximately 20 weeks in an outdoor environment showing of large number of inflorescences.
Figure 2:
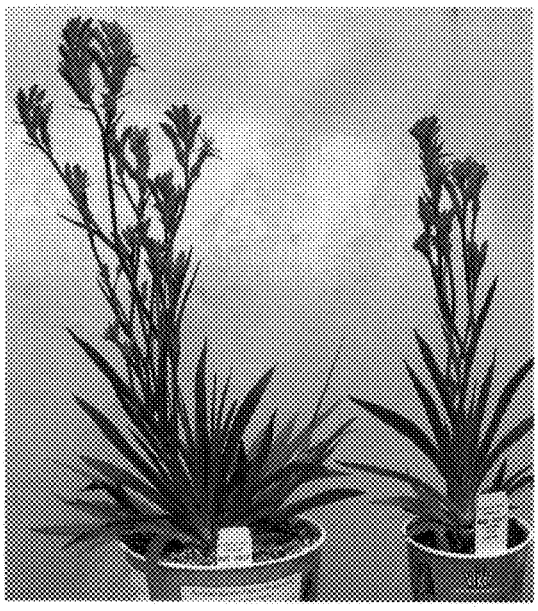
FIG. 2 illustrates a 'Ramboball' plant in a 14 cm pot and 10 cm pot grown for approximately 16 weeks in an outdoor environment showing inflorescence habit and upright plant growth habit
Figure 3:
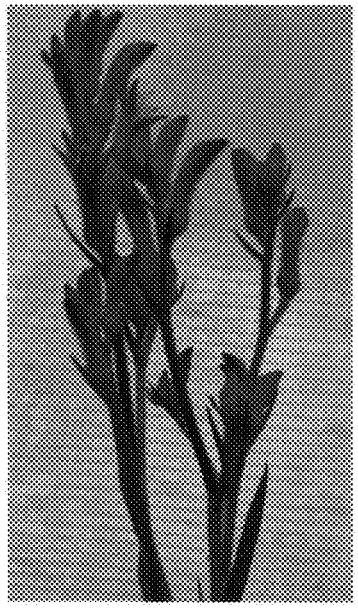
FIG. 3 illustrates a 'Ramboball' inflorescence detail including tertiary branching.
Figure 4:
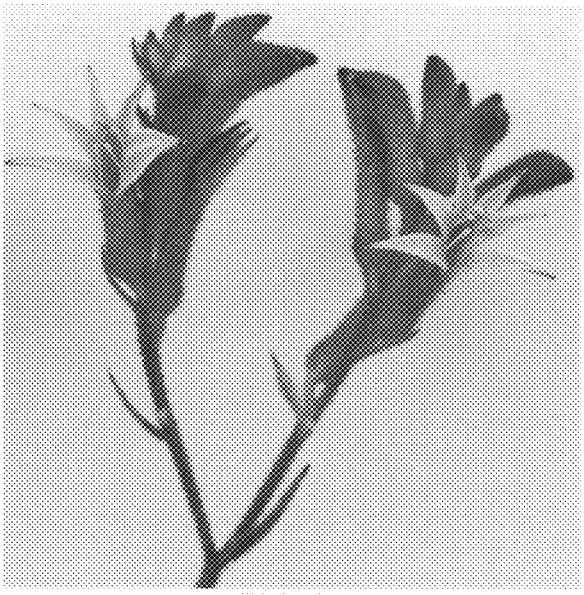
FIG. 4 illustrates 'Ramboball' flowers within the inflorescence showing flower and hair detail including medium reflexing of perianth lobes.

The following is a detailed botanical description of a new and distinct variety of an *Anigozanthos* hybrid ornamental plant known as 'Ramboball'. Plant observations were made on plants grown in Tuggerah, New South Wales, Australia. Unless indicated otherwise, the descriptions disclosed herein are based upon observations made from May 2008 of mature 'Ramboball' plants grown in nursery pots in greenhouse and outdoor growing areas with day temperature ranging from 25° C. to 27° C., night temperatures ranging from 6° C. to 8° C., and light levels ranging from 6 to 8 klux. Plants were grown for about 24 weeks with one plant per 20 cm container. Those skilled in the art will appreciate that certain characteristics will vary with older or, conversely, younger plants. 'Ramboball' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on The Royal Horticultural Society Colour Chart, of The Royal Horticultural Society, London, 2007 edition.

Botanical classification: *Anigozanthos* hybrid cultivar Ramboball.

Parentage:

*Female parent.*—Unnamed proprietary *Anigozanthos* hybrid breeding selection.

*Male parent.*—Unnamed proprietary *Anigozanthos* hybrid breeding selection.

Propagation:

*Type.*—In vitro propagation of micro-plants.

*Time to initiate roots, summer.*—About 7 to 10 days at a temperature of approximately 25° C.

*Time to initiate roots, winter.*—About two weeks at a temperature of approximately 15° C.

*Time to produce a rooted young plant, summer.*—About 45 to 60 days at a temperature of approximately 25° C.

*Time to produce a rooted young plant, winter.*—About 55 to 70 days at a temperature of approximately 15° C.

*Root description.*—Fibrous, freely branching and white in color.

*Rooting habit.*—Freely branching.

Plant description:

*Plant and growth habit.*—Inverted triangle; compact, upright and outwardly spreading plant habit with tertiary branched flowering stems with predominately medium red-colored flowers. Moderately vigorous growth habit.

*Plant height.*—Average plant height including the inflorescence is about 50 cm (range 45 to 60 cm). Average height of foliage only is about 26 cm (range 23 to 30 cm).

*Plant diameter.*—Average plant spread of a mature plant grown in 30 cm nursery pots or field plots in Tuggerah, New South Wales, Australia is about 75 cm (observed summer 2007 through 2008).

*Lateral branch.*—Quantity per plant: About 25. Strength: Strong. Diameter: About 1.8 cm. Length of central internode: About 4 mm. Texture: Smooth, glabrous. Color: 145B.

Foliage description:

*General description.*—The leaf attitude is erect to semi-erect and the degree of leaf curvature is slightly curved. Arrangement: Alternate equitant, simple; sessile.

*Leaves.*—Length: About 18 to 22 cm in a 30 cm pot. Width: About 9 to 12 mm in a 30 cm pot. Shape: Linear to slightly falcate. Apex: Acute. Base: Cauline. Margin: Entire. Texture, upper and lower surfaces: Smooth, glabrous; very weak glaucosity and pubescence on leaf margin is very sparse. Venation pattern: Parallel. Color of the upper and lower surfaces: 146A with indistinguishable venation.

Flower description:

*General description.*—Flowers arranged singly on terminal and axillary racemes. Flowers with tubular perianth; zygomorphic. Terminal flowers are held upright and attitude of flowers gradually changes to a horizontal position proximally. The proximal flowers are the first to open and usually are the only flowers to express perianth lobe reflexure. Flowers not fragrant. Flowers persistent. Length of the lowest inflorescence branch including raceme: About 15 to 20 cm. Number of flowers per inflorescence: About 3 to 4 racemes per inflorescence, each with 10 to 13 flowers greater in length than 3 mm in a 30 cm pot (observed summer 2007 through 2008). Inflorescence height: About 40 to 45 cm. Inflorescence diameter: About 14 to 15 cm. Flower diameter: About 7 mm measured at the base of the lobes and about 2.5 cm across the lobes on an opened flower. Flower height: About 7 mm measured at the base of the lobes and about 20 mm across the lobes on an opened flower.

*Natural flowering season.*—'Ramboball' has a long, almost continuous flowering season under outdoor growing conditions.

*Bud just before opening.*—Shape: Tubular. Length: About 3 cm. Width: About 7 mm. Texture: Tomentose. Color: 146A with dense pubescence colored 59B.

*Perianth.*—Arrangement: Fused elongated tube with six medium reflexed acute lobes; split on lower surface. Appearance: Flare distally. Perianth tube length: 20 to 25 mm. Perianth tube diameter: About 7 mm measured at the base of the lobes. Lobe length: About 8 to 9 mm. Lobe width: About 3 mm at base. Texture, outer surface of perianth tube: Tomentose. Texture, inner surface of perianth tube: Smooth, glabrous. Color: When opening and fully opened, outer surface of perianth tube: 59B. When opening and fully opened, inner surface of perianth tube: 146D. When fully opened, inner surface of perianth lobe 191B.

*Floral bracts.*—Length: Up to 13 cm at stem base and decreasing length to about 2 cm at base of raceme and then 10 to 12 mm for new flowers. Width: Up to 10 mm at stem base and decreasing width to about 4 mm at base of raceme and then 2 to 3 mm for new flowers. Shape: Ensiform tapering to a narrow conduplicate form at the apex. Apex: Narrow acute. Base: Clasping. Margin: Entire with pubescence color 59B. Texture, upper surface: Smooth, glabrous. Texture, lower surface: Tomentose. Color, upper surface: 146A. Color, lower surface: 146A, anthocyanin coloration may be present.

*Peduncle (flowering stems).*—Strength: Strong. Aspect: Upright. Length: About 40 to 45 cm. Diameter at base: About 7.0 mm. Texture: Tomentose. Color of surface: 146B with pubescence color 59B. Color of hairs at junction with floral bracts 59B.

*Pedicels (individual flower stems).*—Length: About 5 mm. Diameter: About 2 mm. Angle: Distally appressed to flowering stems, then about 30° to 45° from flowering stems proximally with the largest, most mature flowers. Strength: Strong. Texture: Tomentose. Color: 146B. Pubescence color: 59B.

*Reproductive organs.*—Stamens: Quantity: 6 per flower. Anther shape: Oblong. Anther size: About 1 mm by 2.5 mm. Anther color: 12A. Pollen amount: Scarce. Pollen color: 12A. Pistils: Quantity: One per flower. Pistil length: About 30 mm. The position of the stigma in relation to the anthers is above. Style length: About 26 mm. Style color: 145A. Stigma shape: Rounded. Stigma color: 144A. Ovary color: 144A with dense pubescence covering colored 59B.

Seed and fruit production: Seed and fruit development have not been observed on plants of the new *Anigozanthos*.

Environmental tolerances: 'Ramboball' plants have exhibited good tolerance to rain and wind and to tolerate temperatures from 1 to about 40° C. 'Ramboball' has moderate to good drought tolerance. 'Ramboball' has moderate to good recovery with watering after severe wilting. 'Ramboball' does well in sandy and gravelly soils.

Disease resistance: 'Ramboball' has been observed to be tolerant to alternaria and rust diseases compared to other *Anigozanthos* varieties.

What is claimed is:

1. A new and distinct cultivar of *Anigozanthos* hybrid plant named 'Ramboball', substantially as herein shown and described.

* * * * *